(12) United States Patent
Maeda

(10) Patent No.: US 10,717,428 B2
(45) Date of Patent: Jul. 21, 2020

(54) CONTROL SYSTEM OF HYBRID VEHICLE

(71) Applicant: TOYOTA JIDOSHA KABUSHIKI KAISHA, Toyota-shi (JP)

(72) Inventor: Eiji Maeda, Ashigarakami-gun (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 76 days.

(21) Appl. No.: 16/217,314

(22) Filed: Dec. 12, 2018

(65) Prior Publication Data
US 2019/0202430 A1 Jul. 4, 2019

(30) Foreign Application Priority Data
Dec. 28, 2017 (JP) .................................. 2017-254469

(51) Int. Cl.
*B60W 20/12* (2016.01)
*B60W 20/13* (2016.01)
*B60W 20/16* (2016.01)
*B60W 20/40* (2016.01)
*B60W 30/188* (2012.01)

(52) U.S. Cl.
CPC ............ *B60W 20/12* (2016.01); *B60W 20/13* (2016.01); *B60W 20/16* (2016.01); *B60W 20/40* (2013.01); *B60W 30/188* (2013.01); *B60W 2552/00* (2020.02)

(58) Field of Classification Search
CPC ............... B60W 20/11; B60W 20/12; B60W 30/18–182; B60W 2552/00; B60W 2552/05; F02D 2200/0611; F02D 2200/0612; F02D 2200/0625; F02D 2200/501; F02D 2200/701; F02N 11/0803

USPC ................. 701/32.4, 103, 123; 123/179.4; 73/114.52, 114.53
See application file for complete search history.

(56) References Cited

U.S. PATENT DOCUMENTS 6,453,731 B1 * 9/2002 Yaegashi ................ B60K 35/00
                                                              73/114.52
8,793,067 B2 * 7/2014 Tsurutani ........... G01C 21/3469
                                                              701/123

(Continued)

FOREIGN PATENT DOCUMENTS

JP        2013-141858         7/2013
JP        2015-202807         11/2015

*Primary Examiner* — Erick R Solis
*Assistant Examiner* — Robert A Werner
(74) *Attorney, Agent, or Firm* — Oblon, McClelland, Maier & Neustadt, L.L.P.

(57) ABSTRACT

A control system comprises a driving mode setting part 41 setting a driving mode, a fuel consumption rate calculating part 42 calculating a first fuel consumption rate when outputting power for driving use and a second fuel consumption rate when storing electric power in the battery, a fuel consumption rate correcting part 43 and a driving region judging part 44. The driving mode setting part sets the driving mode to the EV mode when the first fuel consumption rate is higher than the second fuel consumption rate and sets the driving mode to the engine operating mode when the first fuel consumption rate is lower than the second fuel consumption rate. The fuel consumption rate correcting part performs at least one of first correction raising the first fuel consumption rate and second correction lowering the second fuel consumption rate if the hybrid vehicle is driving through a residential neighborhood.

16 Claims, 10 Drawing Sheets

(56) References Cited

U.S. PATENT DOCUMENTS

2007/0029121 A1* 2/2007 Saitou .................... B60L 58/13
                                                        180/65.285
2013/0166121 A1* 6/2013 Takeuchi ............... B60K 6/445
                                                        701/22

* cited by examiner

COMPARATIVE EXAMPLE 1

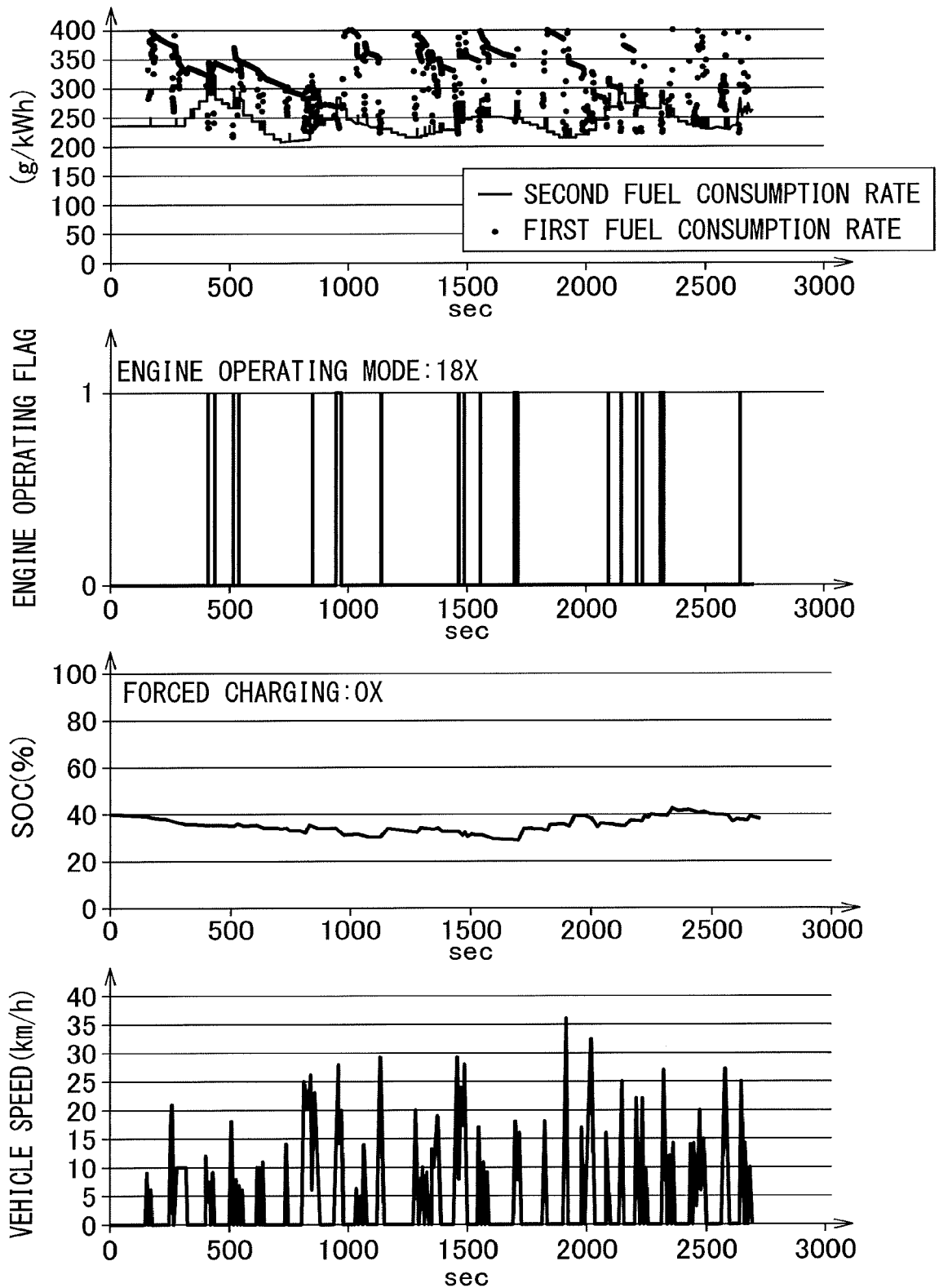

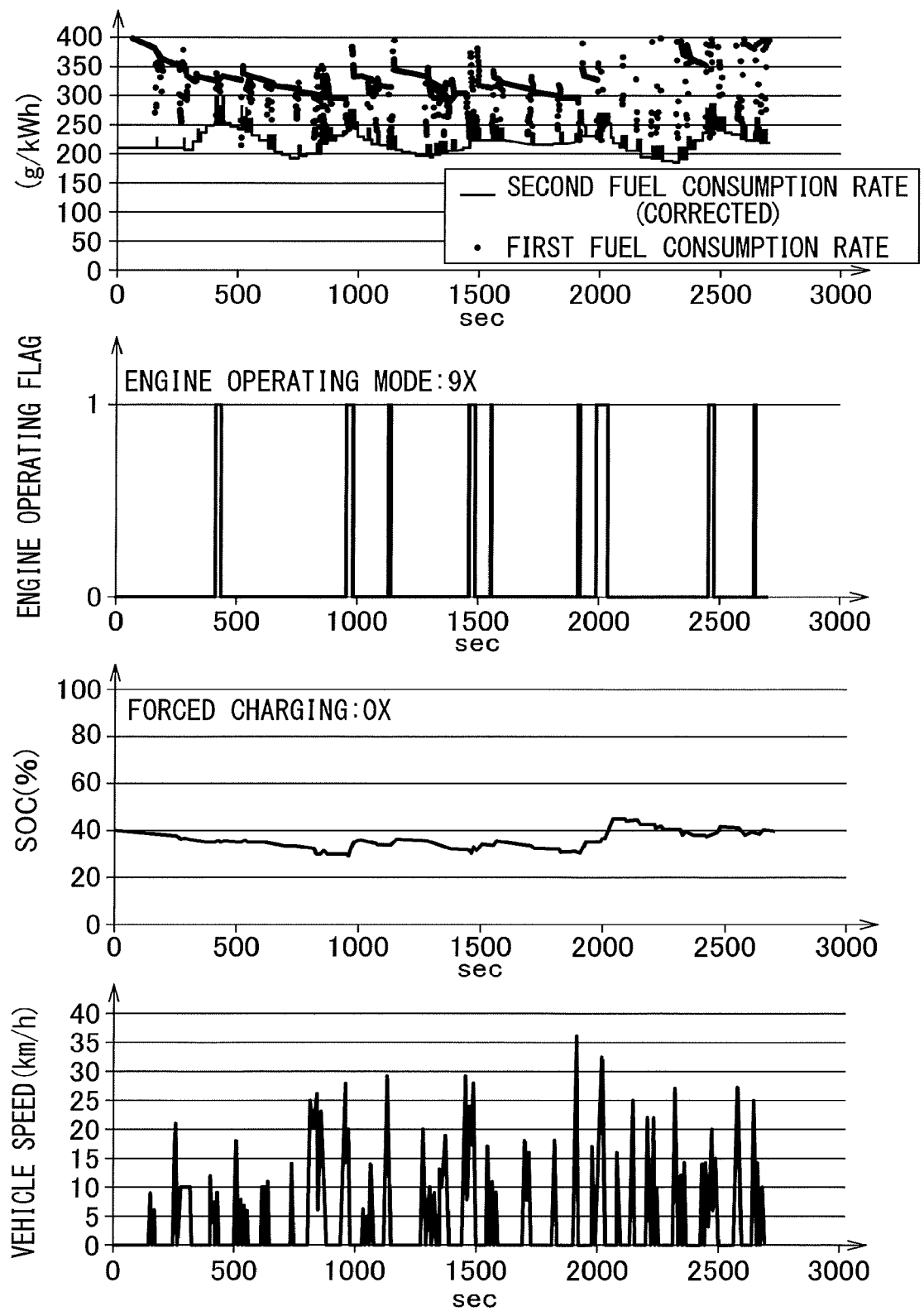

CONTROL SYSTEM OF HYBRID VEHICLE

FIELD

The present invention relates to a control system of a hybrid vehicle.

BACKGROUND

Known in the art has been a hybrid vehicle provided with an internal combustion engine and motor able to output power for driving use, and a battery storing power generated by output of the internal combustion engine and supplying power to the motor (for example, PTLs 1 and 2). In such a hybrid vehicle, the driving mode is switched between an EV mode in which operation of the internal combustion engine is stopped and output of only the motor is used as the power for driving use, and the engine operating mode in which output of the internal combustion engine is used as the power for driving use.

In the vehicle control system described in PTL 1, the driving mode is selected based on the relative magnitude of the first fuel consumption rate of the internal combustion engine when outputting power for driving use and the second fuel consumption rate of the internal combustion engine when storing power in the battery. By doing this, the driving mode with the optimum fuel efficiency becomes selected more often and the fuel efficiency of the internal combustion engine is improved.

Further, in such control, even when the driving output demanded by the driver is small such as at the time of driving at a low speed, the engine operating mode is frequently selected by a change in the accelerator operation etc. For this reason, forced charging of the battery due to a drop in the remaining battery power can be kept from occurring, and the fuel efficiency of the internal combustion engine can be kept from deteriorating due to forced charging.

CITATION LIST

Patent Literature

[PTL 1] Japanese Unexamined Patent Publication No. 2015-202807
[PTL 2] Japanese Unexamined Patent Publication No. 2013-141858

SUMMARY

Technical Problem

However, when the hybrid vehicle is driving through a residential neighborhood at a low speed, if the frequency of intermittent operation of the internal combustion engine rises, the problem of noise due to operation of the internal combustion engine arises. On the other hand, if just selecting the EV mode as the driving mode when driving at a low speed, the frequency of occurrence of forced charging at the time of driving at a low speed becomes greater, and the fuel efficiency of the internal combustion engine greatly deteriorates.

Therefore, in consideration of the above technical problem, an object of the present invention is to provide a control system of a hybrid vehicle able to keep the fuel efficiency of the internal combustion engine from deteriorating while decreasing the noise when driving through a residential neighborhood.

Solution to Problem

The summary of the present disclosure is as follows.

(1) A control system of a hybrid vehicle controlling a hybrid vehicle comprising an internal combustion engine and motor able to output power for driving use, and a battery storing electric power generated using output of the internal combustion engine and supplying electric power to the motor, the control system of the hybrid vehicle comprising: a driving mode setting part configured to set a driving mode of the hybrid vehicle to an EV mode in which an operation of the internal combustion engine is stopped and an output of only the motor is used as power for driving use or an engine operating mode in which the output of the internal combustion engine is used as power for driving use; a fuel consumption rate calculating part configured to calculate a first fuel consumption rate of the internal combustion engine when outputting power for driving use, and a second fuel consumption rate of the internal combustion engine when storing electric power in the battery; a fuel consumption rate correcting part configured to correct at least one of the first fuel consumption rate and the second fuel consumption rate calculated by the fuel consumption rate calculating part; and a driving region judging part configured to judge whether the hybrid vehicle is driving through a residential neighborhood, wherein the driving mode setting part is configured to set the driving mode to the EV mode when the first fuel consumption rate is higher than the second fuel consumption rate, and set the driving mode to the engine operating mode when the first fuel consumption rate is lower than the second fuel consumption rate, and the fuel consumption rate correcting part is configured to perform at least one of first correction raising the first fuel consumption rate and second correction lowering the second fuel consumption rate if the driving region judging part judges that the hybrid vehicle is driving through a residential neighborhood, and not to perform the first correction and the second correction if the driving region judging part judges that the hybrid vehicle is not driving through a residential neighborhood.

(2) The control system of the hybrid vehicle described in above (1), wherein the fuel consumption rate calculating part is configured to calculate the first fuel consumption rate as an amount of fuel consumption of the internal combustion engine per unit driving output of the hybrid vehicle obtained by only the output of the internal combustion engine, and calculate the second fuel consumption rate as an amount of fuel consumption of the internal combustion engine per unit power for all of the electric power stored in the battery.

(3) The control system of the hybrid vehicle described in above (1) or (2), wherein the driving region judging part is configured to judge that the hybrid vehicle is driving through a residential neighborhood if a mean vehicle speed of the hybrid vehicle when the hybrid vehicle has driven over a predetermined distance is equal to or less than a predetermined value.

(4) The control system of the hybrid vehicle described in any one of above (1) to (3), further comprising a time-of-day judging part configured to judge a time of day when the hybrid vehicle is being driven, wherein the fuel consumption rate correcting part is configured to perform at least one of the first correction and the second correction if the driving region judging part judges that the hybrid vehicle is driving through a residential neighborhood and the time of day judged by the time-of-day judging part is early morning or late night, and not to perform the first correction and the second correction if the driving region judging part judges that the hybrid vehicle is not driving through a residential neighborhood or if the time of day judged by the time-of-day judging part is not early morning and late night.

(5) The control system of the hybrid vehicle described in any one of above (1) to (3), wherein the fuel consumption rate correcting part is configured to increase a correction amount of the corrected fuel consumption rate the larger the mean vehicle speed of the hybrid vehicle when the hybrid vehicle has driven over a predetermined distance.

Advantageous Effects of Invention

According to the present invention, there is provided a control system of a hybrid vehicle able to keep the fuel efficiency of the internal combustion engine from deteriorating while decreasing the noise when driving through a residential neighborhood.

BRIEF DESCRIPTION OF DRAWINGS

FIG. 9 shows the results of simulation of Comparative Example 2 in which the fuel consumption rate used for setting the driving mode is not corrected.

FIG. 10 shows the results of simulation of an Example in which the fuel consumption rate used for setting the driving mode is corrected.

DESCRIPTION OF EMBODIMENTS

Figure 1:
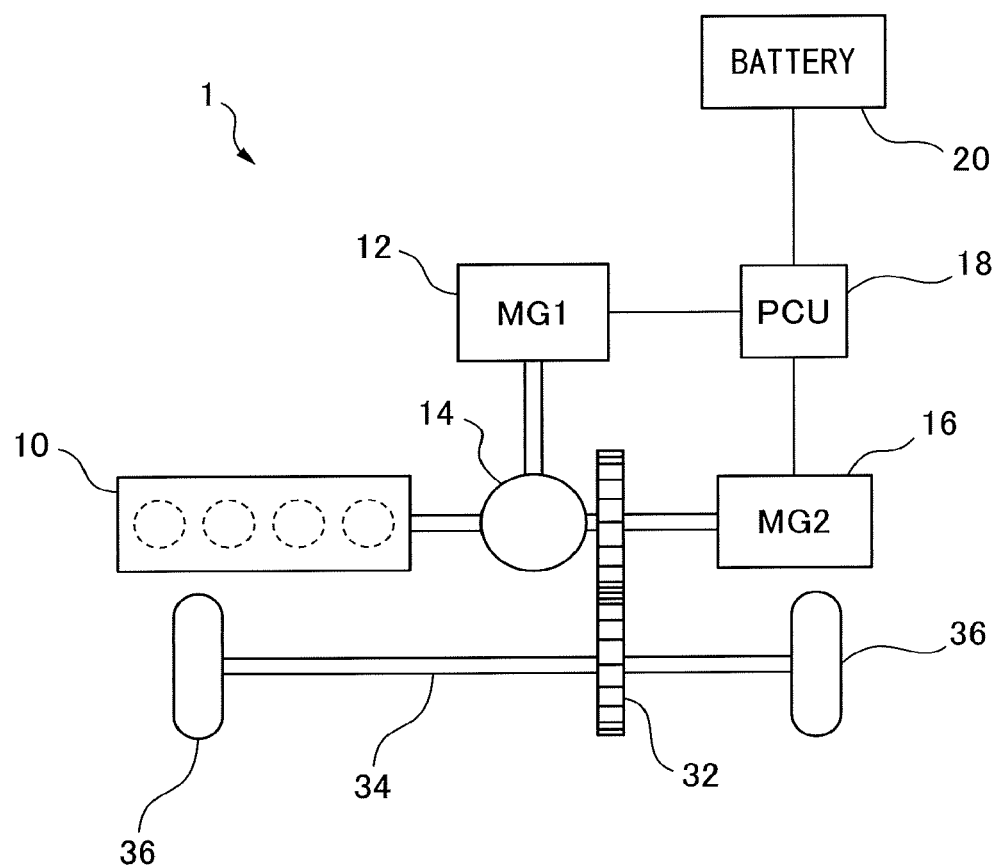
FIG. 1 is a view schematically showing the configuration of a hybrid vehicle according to a first embodiment of the present invention.

Below, referring to the drawings, embodiments of the present invention will be explained in detail. Note that, in the following explanation, similar components are assigned the same reference signs.

First Embodiment

Below, referring to FIG. 1 to FIG. 3, a first embodiment of the present invention will be explained.

<Configuration of Hybrid Vehicle>

FIG. 1 is a view schematically showing the configuration of a hybrid vehicle 1 according to the first embodiment of the present invention. A hybrid vehicle (below, simply referred to as a "vehicle") 1 is provided with an internal combustion engine 10, first motor-generator 12, power distributing mechanism 14, second motor-generator 16, power control unit (PCU) 18, and battery 20.

The internal combustion engine 10 burns an air-fuel mixture of fuel and air in cylinders to output power. The internal combustion engine 10, for example, is a gasoline engine or diesel engine. An output shaft of the internal combustion engine 10 (crankshaft) is mechanically connected to the power distributing mechanism 14, and output of the internal combustion engine 10 is input to the power distributing mechanism 14.

The first motor-generator 12 functions as a generator and motor. The first motor-generator 12 is mechanically connected to the power distributing mechanism 14, and the output of the first motor-generator 12 is input to the power distributing mechanism 14. Further, the first motor-generator 12 is electrically connected to the PCU 18. When the first motor-generator 12 functions as a generator, the electric power generated by the first motor-generator 12 is supplied through the PCU 18 to the second motor-generator 16, battery 20, or second motor-generator 16 and battery 20. On the other hand, when the first motor-generator 12 functions as a motor, the electric power stored in the battery 20 is supplied through the PCU 18 to the first motor-generator 12.

The power distributing mechanism 14 is configured as a known planetary gear mechanism including a sun gear, ring gear, pinion gears, and a planetary carrier. The output shaft of the internal combustion engine 10 is coupled with the planetary carrier, the first motor-generator 12 is coupled with the sun gear, and a speed reducer 32 is coupled with the ring gear. The power distributing mechanism 14 distributes the output of the internal combustion engine 10 to the first motor-generator 12 and the speed reducer 32.

Specifically, when the first motor-generator 12 functions as a generator, the output of the internal combustion engine 10 input to the planetary carrier is distributed to the sun gear coupled with the first motor-generator 12 and the ring gear coupled with the speed reducer 32 in accordance with the gear ratio. The output of the internal combustion engine 10 distributed to the first motor-generator 12 is used to generate electric power by the first motor-generator 12. On the other hand, the output of the internal combustion engine 10 distributed to the speed reducer 32 is transmitted as power for driving use through an axle 34 to the wheels 36. Therefore, the internal combustion engine 10 can output power for driving use. Further, when the first motor-generator 12 functions as a motor, the output of the first motor-generator 12 is supplied through the sun gear and planetary carrier to the output shaft of the internal combustion engine 10 whereby the internal combustion engine 10 is cranked.

The second motor-generator 16 functions as a generator and motor. The second motor-generator 16 is mechanically connected to the speed reducer 32, and the output of the second motor-generator 16 is supplied to the speed reducer 32. The output of the second motor-generator 16 supplied to the speed reducer 32 is transmitted as power for driving use to the wheels 36 through the axle 34. Therefore, the second motor-generator 16 can output power for driving use.

Further, the second motor-generator 16 is electrically connected to the PCU 18. At the time of deceleration or the time of braking of the vehicle 1, the second motor-generator 16 is driven by rotation of the wheels 36, and the second motor-generator 16 functions as a generator. When the second motor-generator 16 functions as a generator, the electric power generated by the second motor-generator 16 is supplied through the PCU 18 to the battery 20. On the other hand, when the second motor-generator 16 functions as a motor, the electric power stored in the battery 20 is supplied through the PCU 18 to the second motor-generator 16.

The PCU 18 is electrically connected to the first motor-generator 12, second motor-generator 16, and battery 20. The PCU 18 includes a booster converter for boosting the voltage of battery 20, an inverter for converting the DC current supplied from the battery 20 to AC current and converting the AC current generated by the first motor-generator 12 or second motor-generator 16 to DC current, etc.

The battery 20 stores the electric power generated by the first motor-generator 12 using the output of the internal combustion engine 10, and the electric power generated by the second motor-generator 16 using the regenerative energy.

<Control System of Hybrid Vehicle>

Figure 2:
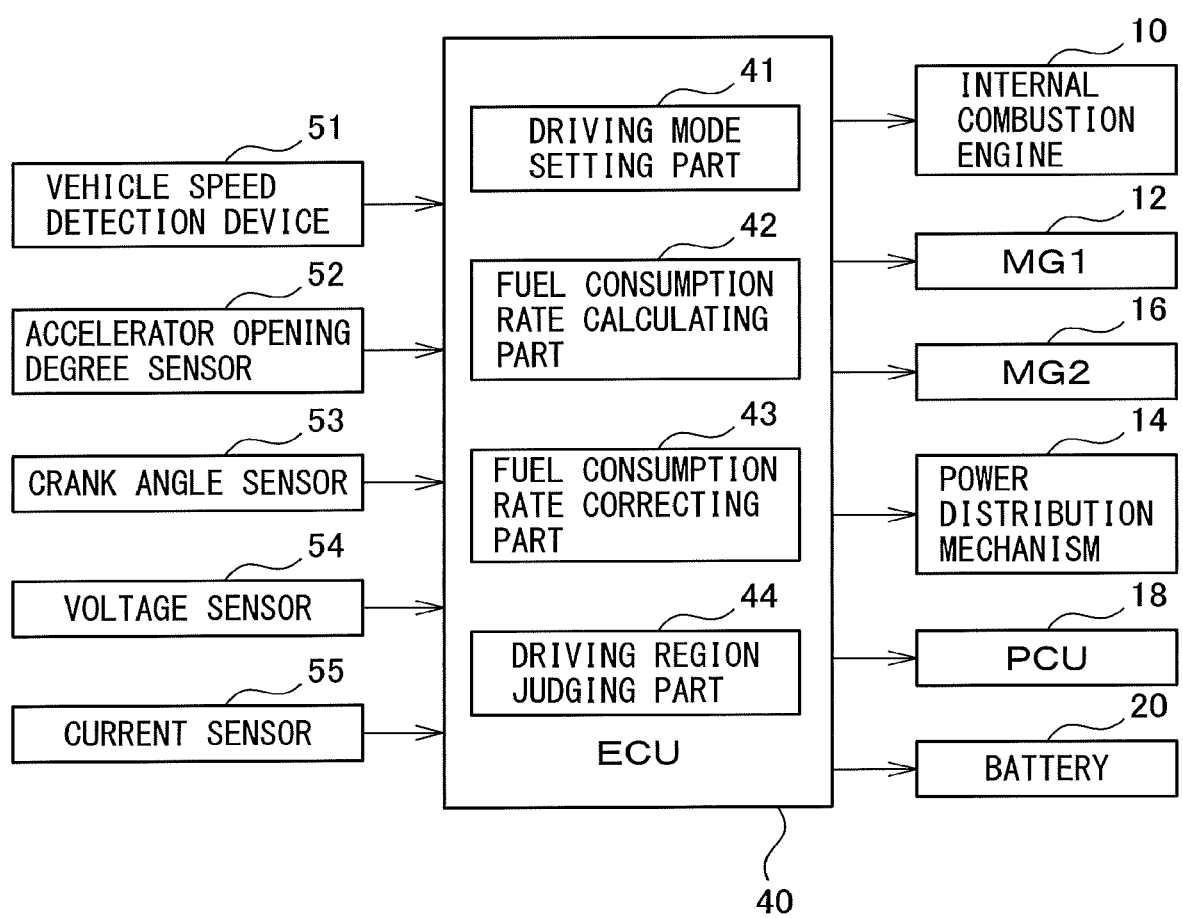
FIG. 2 is a block diagram schematically showing a control system of a hybrid vehicle etc., according to the first embodiment of the present invention.

FIG. 2 is a block diagram schematically showing a control system of the hybrid vehicle etc., according to the first embodiment of the present invention. In the present embodiment, the control system of the vehicle 1 (below, simply referred to as the "control system") is provided with an electronic control unit (ECU) 40, vehicle speed detection device 51, accelerator opening degree sensor 52, crank angle sensor 53, voltage sensor 54, and current sensor 55.

The ECU 40 is a microcomputer provided with a memory such as a read only memory (ROM) and random access memory (RAM), central processing unit (CPU), input port, output port, communication module, etc. In the present embodiment, a single ECU 40 is provided, but a plurality of ECUs may be provided for the different functions. In the present embodiment, the ECU 40 has a driving mode setting part 41, a fuel consumption rate calculating part 42, a fuel consumption rate correcting part 43, and a driving region judging part 44.

The vehicle speed detection device 51 detects the speed of the vehicle 1. The vehicle speed detection device 51 is, for example, a vehicle speed sensor detecting the speed of the vehicle 1 based on the rotational speed of the wheels of the vehicle 1. The vehicle speed detection device 51 is connected to the ECU 40, and the output of the vehicle speed detection device 51 is transmitted to the ECU 40. Note that, the vehicle speed detection device 51 may be a GPS sensor able to detect the speed of the vehicle 1 from the positional information of the vehicle 1 and the elapsed time.

The accelerator opening degree sensor 52 detects the accelerator opening degree corresponding to the depression of an accelerator pedal provided at the vehicle 1. The accelerator opening degree sensor 52 is connected to the ECU 40, and the output of the accelerator opening degree sensor 52 is transmitted to the ECU 40.

The crank angle sensor 53 detects the crank angle of the internal combustion engine 10. The crank angle sensor 53 is connected to the ECU 40, and the output of the crank angle sensor 53 is transmitted to the ECU 40.

The voltage sensor 54 is attached to the battery 20 and detects the voltage across the electrodes of battery 20. The voltage sensor 54 is connected to the ECU 40, and the output of the voltage sensor 54 is transmitted to the ECU 40.

The current sensor 55 is attached to the battery 20 and detects the current flowing through the battery 20. The current sensor 55 is connected to the ECU 40, and the output of the current sensor 55 is transmitted to the ECU 40.

As explained above, as the power source of the vehicle 1, the internal combustion engine 10 and second motor-generator 16 are used. The driving mode setting part 41 sets the driving mode of the vehicle 1 to the EV mode in which operation of the internal combustion engine 10 is stopped and output of only the second motor-generator 16 is used as the power for driving use or the engine operating mode in which the output of the internal combustion engine 10 is used as the power for driving use. In other words, the driving mode setting part 41 switches the driving mode of the vehicle 1 between the EV mode and the engine operating mode.

In the EV mode, operation of the internal combustion engine 10 is stopped and power is supplied from the battery 20 to the second motor-generator 16. The second motor-generator 16 functions as a motor and the output of the second motor-generator 16 is used as the power for driving use.

On the other hand, in the engine operating mode, the internal combustion engine 10 is operated and the output of the internal combustion engine 10 is distributed to the speed reducer 32 and the first motor-generator 12. The output distributed to the speed reducer 32 is used as power for driving use, while the output distributed to the first motor-generator 12 is used for power generation by the first motor-generator 12. The power generated by the first motor-generator 12 is supplied to the second motor-generator 16, battery 20, or second motor-generator 16 and battery 20.

In the engine operating mode, if the power generated by the first motor-generator 12 is supplied to the second motor-generator 16 or the second motor-generator 16 and battery 20, the outputs of the internal combustion engine 10 and second motor-generator 16 are used as power for driving use. Further, when the demanded torque is large such as at the time of rapid acceleration of the vehicle 1, the electric power stored in the battery 20 is also supplied to the second motor-generator 16. Note that, in the engine operating mode, only the output of the internal combustion engine 10 may be used as the power for driving use at all times. Therefore, in the engine operating mode, at least the output of the internal combustion engine 10 is used as power for driving use.

As explained above, in the EV mode, the operation of the internal combustion engine 10 is stopped. Therefore, in the internal combustion engine 10, fuel is not consumed. However, when the battery 20 stores electric power generated using the output of the internal combustion engine 10, fuel is substantially consumed by outputting power for driving use using electric power supplied from the battery 20.

Further, if the time during which the EV mode is maintained becomes longer, the remaining power of the battery 20 falls and the battery 20 is forced charged. That is, the driving mode is forcibly switched from the EV mode to the engine operating mode, and the battery 20 is charged by output of the internal combustion engine 10. At this time, the heat efficiency of the internal combustion engine 10 is ignored. For this reason, if the internal combustion engine 10 is operated at an operating point with a low heat efficiency for forced charging, the fuel efficiency deteriorates. In particular, if forced charging is performed when the vehicle 1 has temporarily stopped, the fuel efficiency greatly deteriorates.

For this reason, with just simply lengthening the driving time in the EV mode, the fuel efficiency of the internal combustion engine 10 cannot be improved. Therefore, in the present embodiment, the driving mode is set considering the heat efficiency of the internal combustion engine 10 at the time of outputting power for driving use, and the heat efficiency of the internal combustion engine 10 at the time of storing electric power in the battery 20. Further, the fuel consumption rate of the internal combustion engine 10 is used as an indicator of the heat efficiency of the internal combustion engine 10. The higher the heat efficiency, the lower the fuel consumption rate becomes.

The fuel consumption rate calculating part 42 calculates the first fuel consumption rate of the internal combustion engine 10 when outputting power for driving use, and the second fuel consumption rate of the internal combustion engine 10 when storing electric power in the battery 20. The unit of the first fuel consumption rate and the second fuel consumption rate is (g/kWh). The specific method of calculation of the first fuel consumption rate and the second fuel consumption rate will be explained later.

The higher the first fuel consumption rate, the greater the amount of fuel used for outputting power for driving use. The higher the second fuel consumption rate, the greater the amount of fuel used for storing electric power in the battery 20. For this reason, when the first fuel consumption rate is higher than the second fuel consumption rate, by setting the driving mode to the EV mode, it is possible to substantially decrease the amount of fuel consumption when driving. On the other hand, when the first fuel consumption rate is lower than the second fuel consumption rate, by setting the driving mode to the engine operating mode, it is possible to substantially decrease the amount of fuel consumption when driving. For this reason, the driving mode setting part 41 sets the driving mode to the EV mode when the first fuel consumption rate is higher than the second fuel consumption rate and sets the driving mode to the engine operating mode when the first fuel consumption rate is lower than the second fuel consumption rate.

If the driving mode is set for optimizing the fuel efficiency in the above way, the driving mode is more frequently switched compared with when the driving mode is set based on the driving state of the vehicle 1. That is, the frequency of intermittent operation of the internal combustion engine 10 rises.

However, if, when the vehicle is driving through a residential neighborhood at a low speed, the frequency of intermittent operation of the internal combustion engine 10 rises, a problem arises with the noise due to the operation of the internal combustion engine 10. On the other hand, if simply selecting the EV mode as the driving mode when driving at a low speed, the frequency of occurrence of forced charging becomes greater when driving at a low speed and the fuel efficiency of the internal combustion engine 10 greatly deteriorates. Therefore, in the present embodiment, if it is judged that the vehicle 1 is driving through a residential neighborhood, the fuel consumption rate is corrected so as to lower the frequency of intermittent operation of the internal combustion engine 10.

The driving region judging part 44 judges whether the vehicle 1 is driving through a residential neighborhood. For example, the driving region judging part 44 judges that the vehicle 1 is driving through a residential neighborhood if the mean speed of the vehicle 1 when the vehicle 1 has driven a predetermined distance is equal to or less than a predetermined value. The predetermined value is, for example, 35 km/h to 45 km/h. The predetermined distance is a predetermined distance up to the current location or distance over which the vehicle 1 has been driven during a predetermined time up to the current time. The mean speed of the vehicle 1 is, for example, calculated as the mean value of the vehicle speed detected by the vehicle speed detection device 51 when the vehicle 1 has been driven over the predetermined distance. Note that, the mean speed of the vehicle 1 may be calculated as a value obtained by dividing the predetermined distance by a time required for driving over it.

Note that, the driving region judging part 44 may judge that the vehicle 1 is driving through a residential neighborhood if the acceleration of the vehicle 1 after temporarily stopping is equal to or less than a predetermined value. The acceleration of the vehicle 1 is calculated as the change over time of the vehicle speed detected by the vehicle speed detection device 51.

Further, if a navigation system having a GPS receiver and map information is provided at the vehicle 1, the driving region judging part 44 may make the above judgment based on the current positional information of the vehicle 1 acquired from the navigation system. For example, the driving region judging part 44 may judge that the vehicle 1 is driving through a residential neighborhood if the width of the road over which the vehicle 1 is being driven or the speed limit is equal to or less than a predetermined value. Further, the driving region judging part 44 may judge that the vehicle 1 is driving through a residential neighborhood if the number of intersections in a predetermined range in the surroundings of the vehicle 1 is equal to or larger than a predetermined value. Note that, the current positional information of the vehicle 1 may be acquired by communication with a data center at the outside of the vehicle 1, vehicle-vehicle communication between the vehicle 1 and another vehicle, road-vehicle communication through a roadside apparatus, etc.

Further, if a surrounding information detection device detecting information on the surroundings of the vehicle 1 is provided at the vehicle 1, the above judgment may be performed based on the information acquired from the surrounding information detection device. For example, the driving region judging part 44 may judge that the vehicle 1 is driving through a residential neighborhood if housing is detected by the surrounding information detection device. The surrounding information detection device is, for example, a LIDAR (laser imaging detection and ranging), milliwave radar sensor, external camera, or combination of the same.

Further, when a sound level detection device for detecting the level of sound in the surroundings of the vehicle 1 is provided at the vehicle 1, the driving region judging part 44 may judge that the vehicle 1 is driving through a residential neighborhood if the sound detected by the sound level detection device is equal to or less than a predetermined value. Further, if a quiet noise switch pushed by the driver when the driver desires to reduce the driving noise of the vehicle 1 is provided at the vehicle 1, the driving region judging part 44 judges that the vehicle 1 is driving through a residential neighborhood if the quiet noise switch is pushed by the driver.

Further, the driving region judging part 44 may combine the above methods to judge whether the vehicle 1 is driving through a residential neighborhood.

The fuel consumption rate correcting part 43 corrects at least one of the first fuel consumption rate and the second fuel consumption rate calculated by the fuel consumption rate calculating part 42. If raising the first fuel consumption rate or lowering the second fuel consumption rate, the EV mode becomes easier to select as the driving mode. If raising the first fuel consumption rate and lowering the second fuel consumption rate, the engine operating mode also becomes harder to select as the driving mode.

For this reason, the fuel consumption rate correcting part 43 performs at least one of first correction raising the first fuel consumption rate and second correction lowering the second fuel consumption rate if the driving region judging part 44 judges that the vehicle 1 is driving through a residential neighborhood. Further, the fuel consumption rate correcting part 43 does not perform the first correction and the second correction if the driving region judging part 44 judges that the vehicle 1 is not driving through a residential neighborhood.

Due to the above correction, the engine operating mode become harder to select as the driving mode and the frequency of intermittent operation of the internal combustion engine 10 when the vehicle 1 is driving through a residential neighborhood falls. For this reason, it is possible to decrease the noise when driving through a residential neighborhood. Further, even when the above correction is performed, basically, the driving mode is selected so that the fuel efficiency is improved. For this reason, the fuel efficiency can be kept from deteriorating.

<Processing for Setting Driving Mode>

Below, referring to the flow chart of FIG. 3, the control for setting the driving mode of the vehicle 1 will be explained in detail. FIG. 3 is a flow chart showing a control routine of processing for setting the driving mode in the first embodiment of the present invention. The present control routine is performed by the ECU 40 at predetermined time intervals after the ignition switch of the vehicle 1 is turned on.

First, at step S101, the fuel consumption rate calculating part 42 calculates the first fuel consumption rate F1 of the internal combustion engine 10 when outputting the power for driving use. Specifically, the fuel consumption rate calculating part 42 calculates the first fuel consumption rate F1 as the amount of fuel consumption of the internal combustion engine 10 per unit driving output of the vehicle 1 obtained by only output of the internal combustion engine 10.

The first fuel consumption rate changes according to the operating point (driving point) of the internal combustion engine 10 specified by the demanded torque and the engine speed. For this reason, the fuel consumption rate calculating part 42, for example, uses a map showing the relationship between the demanded torque and engine speed and the first fuel consumption rate to calculate the first fuel consumption rate from the demanded torque and the engine speed. Note that, as the demanded torque and the engine speed, the current values are respectively used.

The fuel consumption rate calculating part 42, for example, uses a map showing the relationship of the accelerator opening degree and vehicle speed and the demanded torque to calculate the demanded torque from the accelerator opening degree and vehicle speed. The accelerator opening degree is detected by the accelerator opening degree sensor 52, while the vehicle speed is detected by the vehicle speed detection device 51. The engine speed is calculated based on the output of the crank angle sensor 53.

Next, at step S102, the fuel consumption rate calculating part 42 calculates the second fuel consumption rate F2 of the internal combustion engine 10 when storing electric power in the battery 20. Specifically, the fuel consumption rate calculating part 42 calculates the second fuel consumption rate F2 as the amount of fuel consumption of the internal combustion engine 10 per unit power for all power stored in the battery 20.

The fuel consumption rate calculating part 42 calculates the total amount of electric power "a" stored in the battery 20 and the amount of fuel consumption J consumed in the internal combustion engine 10 for storing the total amount of power "a" in the battery 20 and divides the amount of fuel consumption J by the total amount of power "a" to calculate the second fuel consumption rate F2.

The total amount of power "a" is calculated by the following formula (1):

$$a = a_b + d + r - c \quad (1)$$

Here, $a_b$ is the total amount of electric power calculated at step S102 the previous time, "d" is the amount of electric power newly generated using the output of the internal combustion engine 10, "r" is the amount of electric power newly generated using the regenerative energy, and "c" is the amount of electric power newly supplied from the battery 20 to the second motor-generator 16.

The amount of output electric power "c" is calculated by the following formula (2):

$$c = V \times I \times T \quad (2)$$

Here, V is the voltage of the battery 20 detected by the voltage sensor 54 when electric power is supplied from the battery 20, I is the current of the battery 20 detected by the current sensor 55 when electric power is supplied from the battery 20, and T is the time when electric power is supplied from the battery 20 (1/3600 sec).

When electric power is supplied to the battery 20, that is, when the battery 20 is charged, the current I becomes a negative value. For this reason, the amount of electric power "d" generated by the internal combustion engine 10 is calculated as the absolute value of the value calculated by the right side of the above formula (2) when the output of the internal combustion engine 10 is larger than zero and the current I is a negative value. Further, the amount of electric power "r" generated by the regenerative energy is calculated as the absolute value of the value calculated by the right side of the above formula (2) when the output of the internal combustion engine 10 is zero and the current I is a negative value.

The value of the total amount of electric power "a" the previous time plus the amount of change of the total amount of electric power (d+r-c) is made the new total amount of electric power "a". The initial value of the total amount of electric power "a" is determined in advance. Note that, total amount of electric power "a" may be calculated based on the state of charge (SOC) of the battery 20. The state of charge SOC is calculated based on the output of the voltage sensor 54 etc.

The amount of fuel consumption J is calculated by the following formula (3):

$$J = J_b + G \times d - F2_b \times c \quad (3)$$

Here, $J_b$ is the amount of fuel consumption calculated at step S102 the previous time, G is the fuel consumption rate of the internal combustion engine 10 when electric power "d" has been stored in the battery 20, and $F2_b$ is the second fuel consumption rate calculated at step S102 the previous time. The fuel consumption rate G is calculated by a method similar to the first fuel consumption rate F1 based on the operating point of the internal combustion engine 10 when the electric power "d" is stored in the battery 20. The initial values of the amount of fuel consumption J and the second fuel consumption rate F2 are determined in advance.

The second fuel consumption rate F2 is calculated by the following formula (4):

$$F2 = J/a \quad (4)$$

Next, at step S103, the driving region judging part 44 uses any of the methods described above to judge whether the vehicle 1 is driving through a residential neighborhood. If at step S103 it is judged that the vehicle 1 is driving through a residential neighborhood, the present control routine proceeds to step S104.

At step S104, the fuel consumption rate correcting part 43 corrects the second fuel consumption rate F2. Specifically, the fuel consumption rate correcting part 43 lowers the second fuel consumption rate F2 calculated at step S102. For example, the fuel consumption rate correcting part 43 subtracts the correction amount β1 from the second fuel consumption rate F2 (F2←F2−β1). The correction amount β1 is determined in advance and is set to a positive value. Note that, the fuel consumption rate correcting part 43 may divide the second fuel consumption rate F2 by the correction amount β2 (F2←F2/β2). The correction amount β2 is determined in advance and is set to a value larger than 1.

On the other hand, if at step S103 it is judged that the vehicle 1 is not driving through a residential neighborhood, the present control routine skips step S104. That is, the second fuel consumption rate F2 is not corrected.

After step S103 or step S104, at step S105, the driving mode setting part 41 judges whether the first fuel consumption rate F1 is higher than the second fuel consumption rate F2. If at step S105 it is judged that the first fuel consumption rate F1 is higher than the second fuel consumption rate F2, the present control routine proceeds to step S106.

At step S106, the driving mode setting part 41 sets the driving mode to the EV mode. After step S106, the present control routine ends.

On the other hand, if at step S105 it is judged that the first fuel consumption rate F1 is equal to or less than the second fuel consumption rate F2, the present control routine proceeds to step S107. At step S107, the driving mode setting part 41 sets the driving mode to the engine operating mode. After step S107, the present control routine ends.

Note that, the method of calculation of first fuel consumption rate F1 and the second fuel consumption rate is not necessarily limited to the above method. For example, the fuel consumption rate calculating part 42 may calculate the first fuel consumption rate based on the demanded torque and the mean value of the engine speed when the vehicle 1 has been driven a predetermined distance. Further, the fuel consumption rate calculating part 42 may calculate the second fuel consumption rate F2 as the amount of fuel consumption of the internal combustion engine 10 per unit power for the electric power stored in the battery 20 when the vehicle 1 has been driven a predetermined distance. The predetermined distance is a predetermined distance up to the current position or the distance by which the vehicle 1 is driven in a predetermined time up to the current time.

Further, at step S104, the fuel consumption rate correcting part 43 may correct the first fuel consumption rate F1 instead of the second fuel consumption rate. In this case, the fuel consumption rate correcting part 43 raises the first fuel consumption rate F1 calculated at step S101. For example, the fuel consumption rate correcting part 43 adds the correction amount β3 to the first fuel consumption rate F1 (F1←F1+β3). The correction amount β3 is determined in advance and is set to a positive value. Note that, the fuel consumption rate correcting part 43 may multiply the correction amount β4 with the first fuel consumption rate F1 (F1←F1×β4). The correction amount β4 is determined in advance and is set to a value larger than "1".

Further, at step S104, the fuel consumption rate correcting part 43 may correct the first fuel consumption rate F1 and the second fuel consumption rate F2. In this case, the fuel consumption rate correcting part 43 uses the method as described above to raise the first fuel consumption rate F1 and lower the second fuel consumption rate F2.

Further, in the present embodiment, when the first fuel consumption rate F1 and the second fuel consumption rate F2 are equal, the driving mode is set to the engine operating mode. However, the driving mode may be set to EV mode when the first fuel consumption rate F1 and the second fuel consumption rate F2 are equal. That is, at step S105, the driving mode setting part 41 may judge whether the first fuel consumption rate F1 is equal to or larger than the second fuel consumption rate F2.

Note that, if the driving mode is set by the present control routine, the engine operating mode is selected by a suitable frequency even when driving at a low speed, so almost no forced charging occurs. However, when the state of charge SOC is equal to or less than the threshold value (for example, 20 to 40%), forced charging is performed.

Second Embodiment

The control system of a hybrid vehicle according to a second embodiment is basically similar in configuration and control to the control system of the hybrid vehicle according to the first embodiment except for the points explained below. For this reason, below, the second embodiment of the present invention will be explained focusing on parts different from the first embodiment.

Noise in a residential neighborhood is problematic particularly in the early morning or late night. For this reason, in the second embodiment, when the vehicle 1 is driving through a residential neighborhood in the early morning or late night, the fuel consumption rate is corrected so as to lower the frequency of intermittent operation of the internal combustion engine 10. By doing this, the time when the fuel consumption rate is not corrected, that is, the time when the driving mode is selected for optimizing the fuel efficiency, can be lengthened and the fuel efficiency of the internal combustion engine 10 can be kept from deteriorating more.

Figure 4:
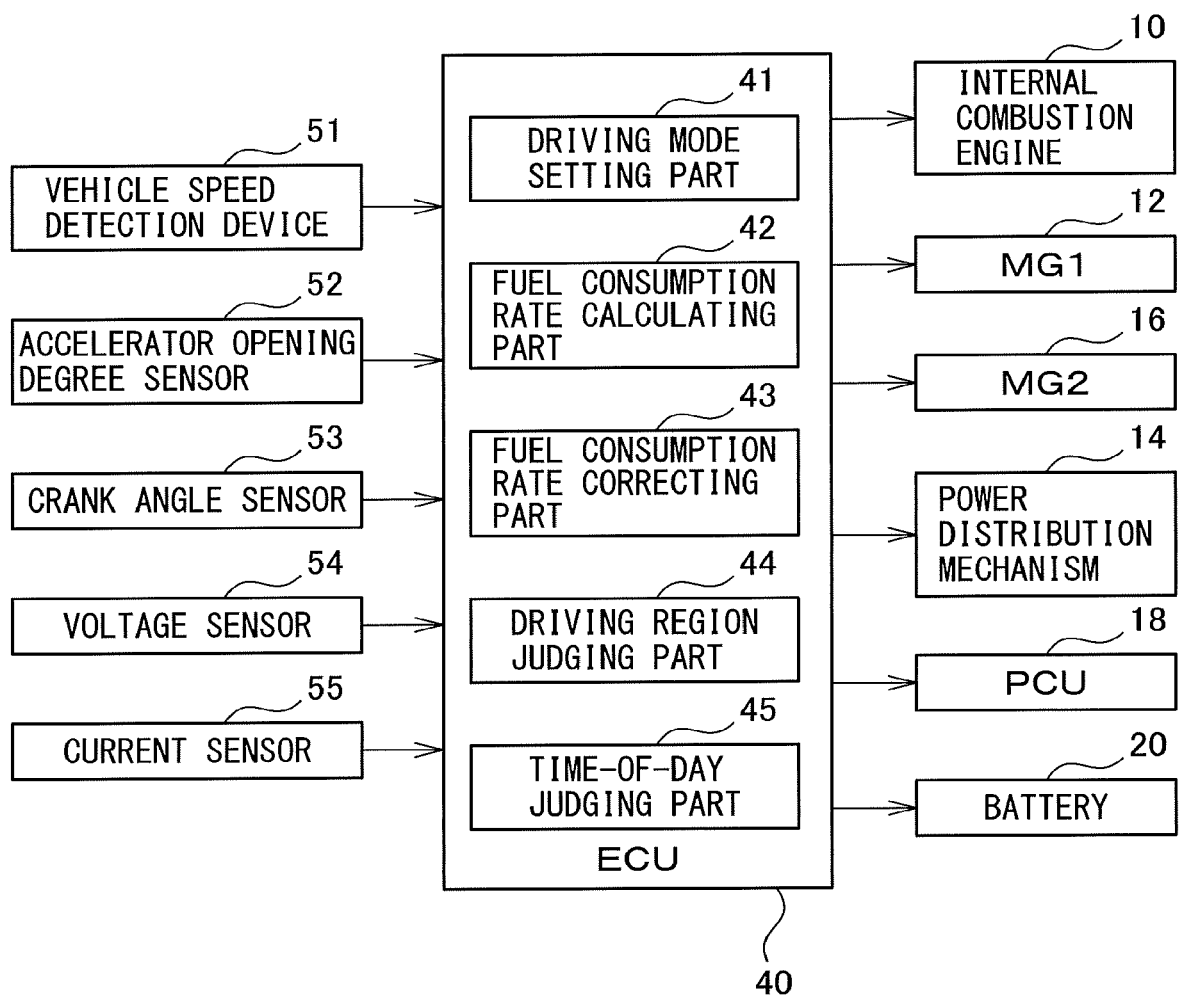
FIG. 4 is a block diagram schematically showing a control system of a hybrid vehicle etc., according to a second embodiment of the present invention.

FIG. 4 is a block diagram schematically showing the control system of the hybrid vehicle etc. according to the second embodiment of the present invention. In the second embodiment, the ECU 40 has a driving mode setting part 41, fuel consumption rate calculating part 42, fuel consumption rate correcting part 43, driving region judging part 44, and time-of-day judging part 45.

The time-of-day judging part 45 judges the time of day when the vehicle 1 is being driven. For example, the time-of-day judging part 45 judges that the time of day when the vehicle 1 is being driven is early morning or late night when the time shown by the clock provided at the vehicle 1 is a predetermined time of day (for example, 10:00 pm to 7:00 am). Note that, if an illumination sensor detecting the illumination of the surroundings of the vehicle 1 is provided at the vehicle 1, the time-of-day judging part 45 may judge that the time of day when the vehicle 1 is being driven is early morning or late night when the output of the illumination sensor is equal to or less than a predetermined value.

The fuel consumption rate correcting part 43 performs at least one of first correction raising the first fuel consumption rate and second correction lowering the second fuel consumption rate if the driving region judging part 44 judges that the vehicle 1 is driving through a residential neighborhood and the time of day judged by the time-of-day judging part 45 is early morning or late night. Further, the fuel consumption rate correcting part 43 does not perform the first correction and the second correction if the driving region judging part 44 judges that the vehicle 1 is not driving through a residential neighborhood or when the time of day judged by the time-of-day judging part 45 is not early morning and late night.

<Processing for Setting Driving Mode>

Figure 5:
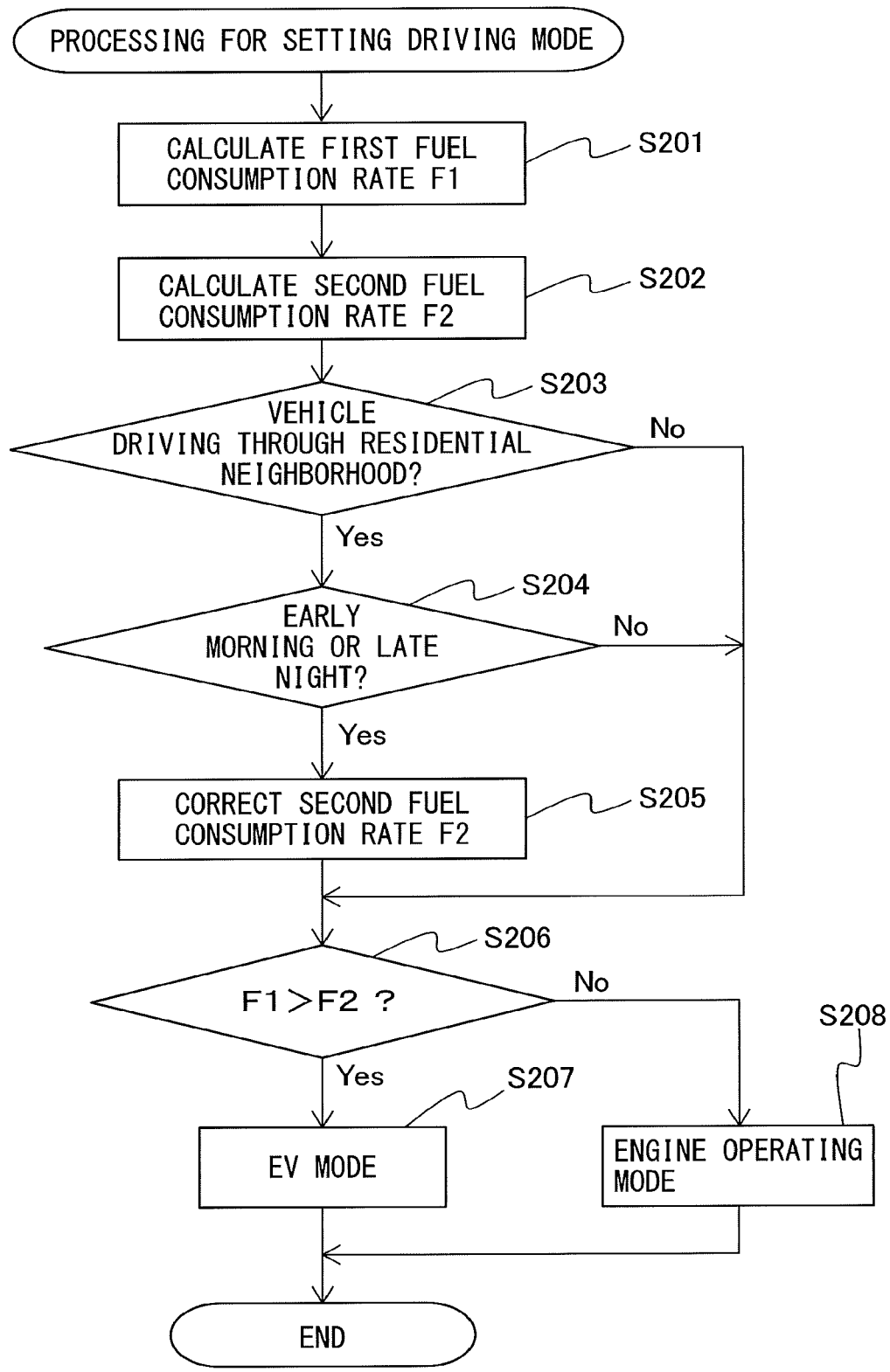
FIG. 5 is a flow chart showing a control routine of processing for setting a driving mode in the second embodiment of the present invention.

FIG. 5 is a flow chart showing a control routine of processing for setting the driving mode in the second embodiment of the present invention. The present control routine is performed by the ECU 40 at predetermined time intervals after the ignition switch of the vehicle 1 is turned on.

Figure 3:
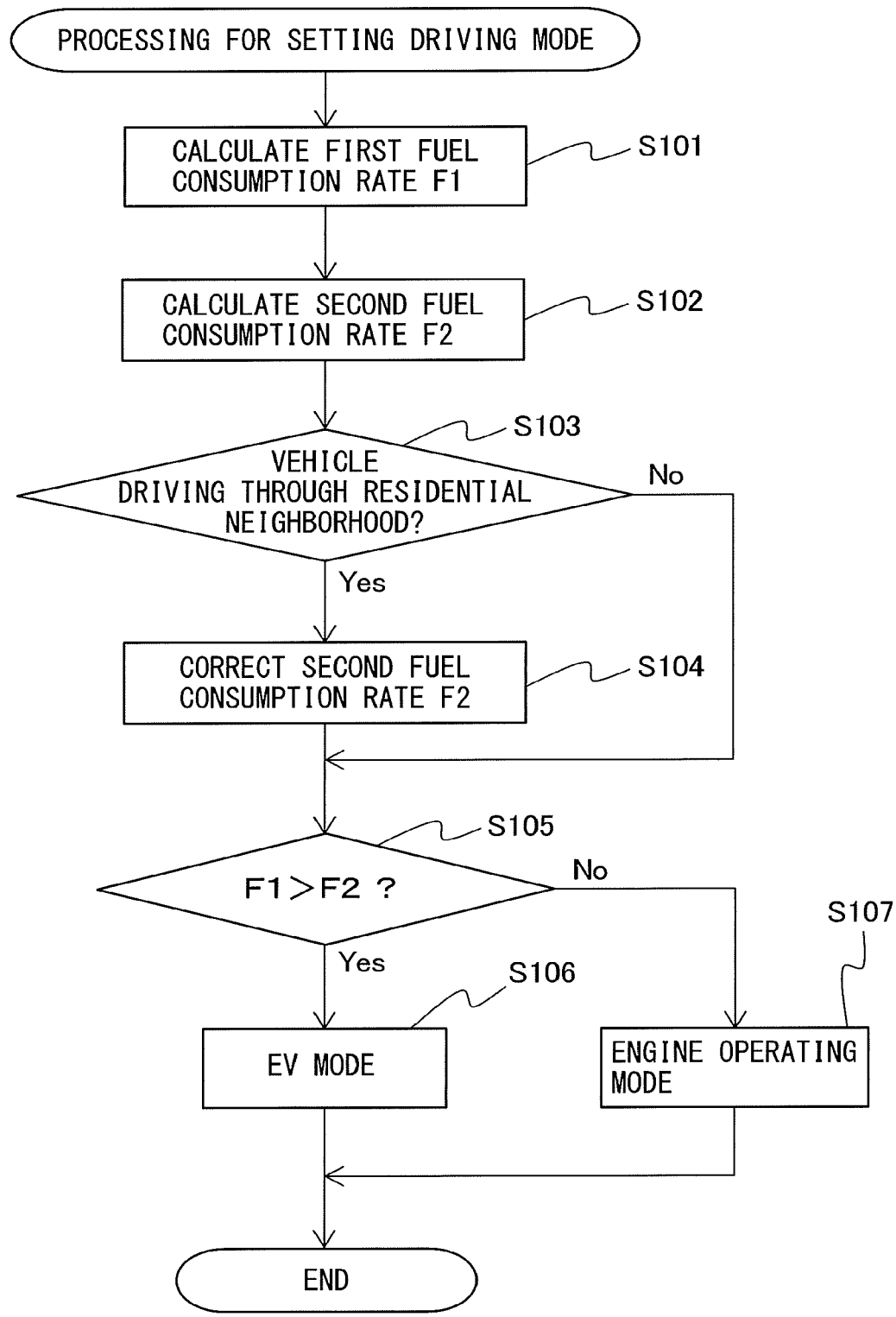
FIG. 3 is a flow chart showing a control routine of processing for setting a driving mode in the first embodiment of the present invention.

Step S201 to step S203 are similar to step S101 to step S103 of FIG. 3, so explanations will be omitted. If it is judged at step S203 that the vehicle 1 is driving through a residential neighborhood, the present control routine proceeds to step S204.

At step S204, the time-of-day judging part 45 judges whether the time of day when the vehicle 1 is being driven is early morning or late night. If it is judged that the time of day when the vehicle 1 is being driven is early morning or late night, the present control routine proceeds to step S205. At step S205, in the same way as step S104 of FIG. 3, the second fuel consumption rate F2 is corrected. On the other hand, if the time of day when the vehicle 1 is being driven is not early morning and late night, the present control routine proceeds to step S206. That is, the second fuel consumption rate F2 is not corrected.

Step S206 to step S208 are similar to step S105 to step S107 of FIG. 3, so explanations will be omitted. Note that, the control routine of FIG. 5 can be changed in the same way as the control routine of FIG. 3.

Third Embodiment

The control system of a hybrid vehicle according to a third embodiment is basically similar in configuration and control to the control system of the hybrid vehicle according to the first embodiment except for the points explained below. For this reason, below, the third embodiment of the present invention will be explained focusing on parts different from the first embodiment.

When the vehicle 1 is driving through a residential neighborhood, basically, the greater the speed of the vehicle 1, the lower the first fuel consumption rate of the internal combustion engine 10 when outputting power for driving use and the easier it becomes to select the engine operating mode as the driving mode. On the other hand, the smaller the speed of the vehicle 1, the higher the first fuel consumption rate and the easier it becomes to select the EV mode as the driving mode.

If the frequency of the engine operating mode becomes too high, the noise of the vehicle 1 increases. On the other hand, if the frequency of the engine operating mode is too low, forced charging occurs and the fuel efficiency of the internal combustion engine 10 greatly deteriorates.

For this reason, in the third embodiment, the fuel consumption rate correcting part 43 increases the correction amount of the corrected fuel consumption rate the greater the mean speed of the vehicle 1 when the vehicle 1 is driven over a predetermined distance (below, simply referred to as the "mean vehicle speed"). The "predetermined distance" is a predetermined distance up to the current position or the distance over which the vehicle 1 is driven in a predetermined time up to the current time. The mean vehicle speed is calculated as the mean value of the vehicle speed detected by the vehicle speed detection device 51 when, for example, the vehicle 1 is driven over the predetermined distance. Note that, the mean vehicle speed may be calculated as the value obtained by dividing a predetermined distance by the time required for driving over that predetermined distance.

If increasing the correction amount of the fuel consumption rate, the EV mode becomes easier to select as the driving mode. For this reason, by setting the correction amount of the fuel consumption rate as explained above, it is possible to set the correction amount of the fuel consumption rate so as to keep the frequency of the engine operating mode from fluctuating in accordance with the vehicle speed. By doing this, it is possible to more effectively keep the fuel efficiency of the internal combustion engine 10 from deteriorating while reducing the noise when driving through a residential neighborhood.

<Processing for Setting Driving Mode>

Figure 6:
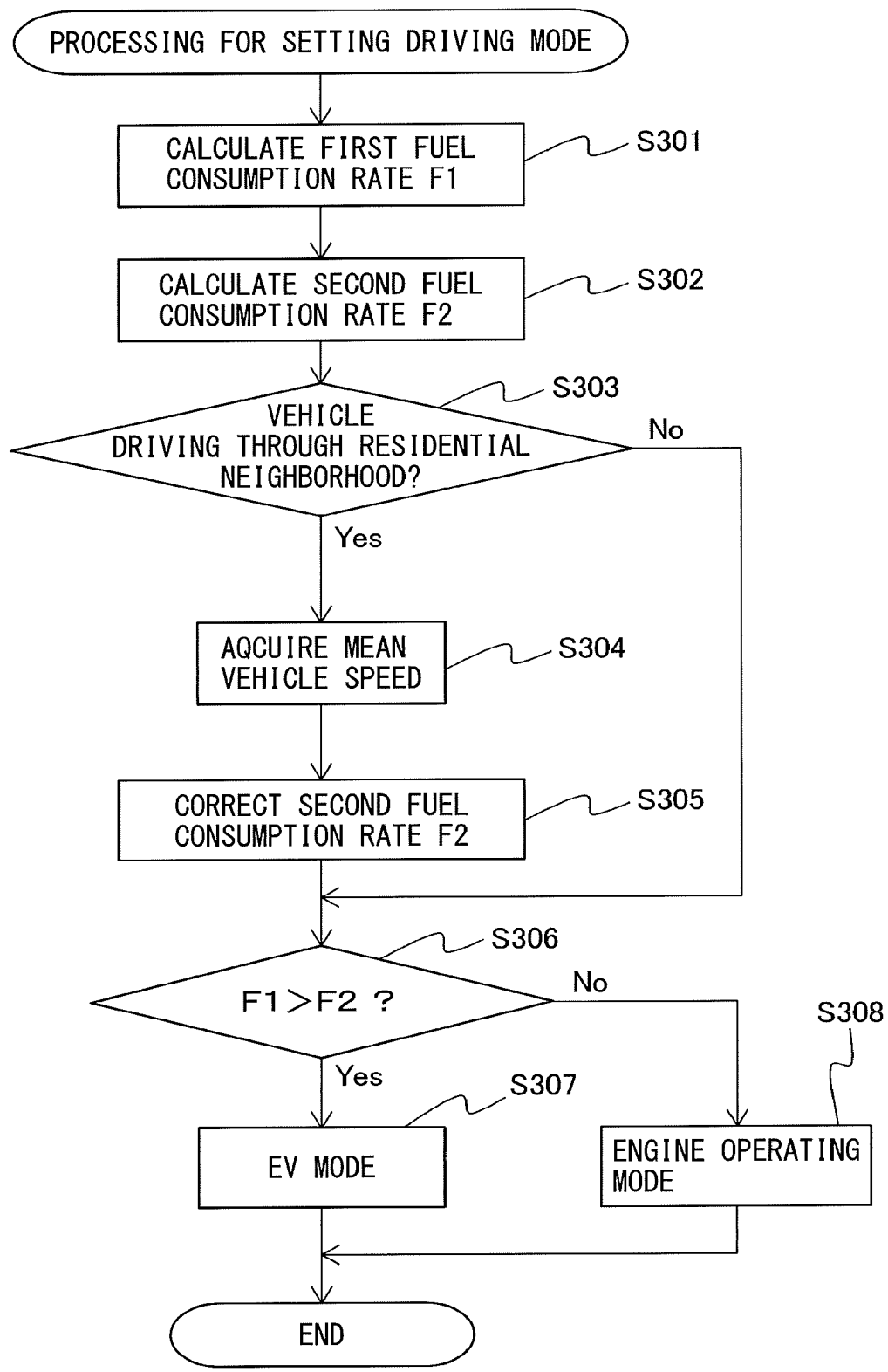
FIG. 6 is a flow chart showing a control routine of processing for setting a driving mode in a third embodiment of the present invention.

FIG. 6 is a flow chart showing a control routine of processing for setting the driving mode in the third embodiment of the present invention. The present control routine is performed by the ECU 40 at predetermined time intervals after the ignition switch of the vehicle 1 is turned ON.

Step S301 to step S303 are similar to step S101 to step S103 of FIG. 3, so explanations will be omitted. If it is judged at step S303 that the vehicle 1 is driving through a residential neighborhood, the present control routine proceeds to step S304.

At step S304, the fuel consumption rate correcting part 43 acquires the mean vehicle speed. Next, at step S305, the fuel consumption rate correcting part 43 corrects the second fuel consumption rate F2. Specifically, the fuel consumption rate correcting part 43 lowers the second fuel consumption rate F2 calculated at step S302. At this time, the fuel consumption rate correcting part 43 increases the correction amount of the second fuel consumption rate F2 the greater the mean vehicle speed.

Figure 7:
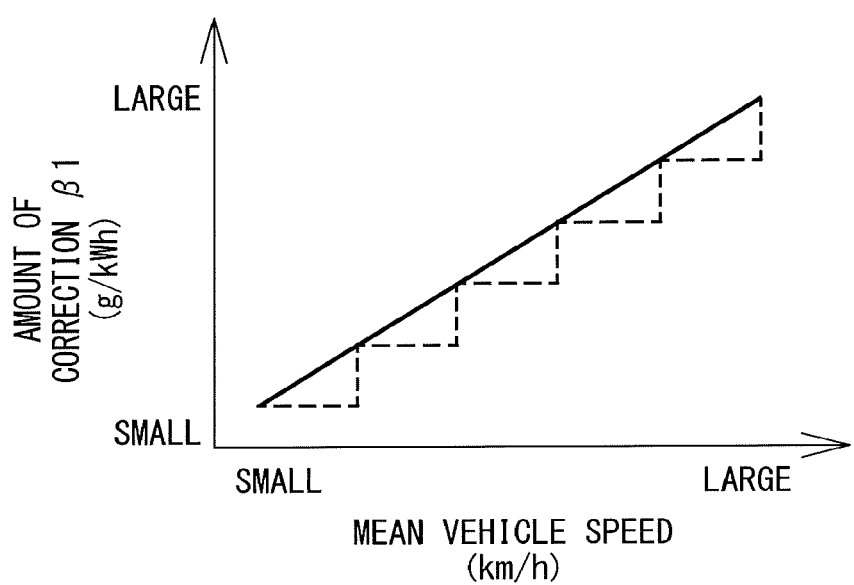
FIG. 7 is a map showing a relationship between a mean speed of a hybrid vehicle and a correction amount of a second fuel consumption rate.

For example, the fuel consumption rate correcting part 43 subtracts a positive correction amount $\beta 1$ from the second fuel consumption rate F2. At this time, the fuel consumption rate correcting part 43 increases the correction amount $\beta 1$ the greater the mean vehicle speed. The fuel consumption rate correcting part 43, for example, uses a map such as shown in FIG. 7 to set the correction amount $\beta 1$ based on the mean vehicle speed. In this map, the correction amount $\beta 1$ is shown as a function of the mean vehicle speed. As shown by the solid line in FIG. 7, the correction amount $\beta 1$ is made larger linearly as the mean vehicle speed becomes larger. Note that, the correction amount $\beta 1$ may be made larger in stages (in steps) as the mean vehicle speed becomes greater.

Note that, the fuel consumption rate correcting part 43 may divide the second fuel consumption rate F2 by a correction amount $\beta 2$ larger than 1. In this case as well, the fuel consumption rate correcting part 43 increases the correction amount $\beta 2$ the greater the mean vehicle speed. The correction amount $\beta 2$ is set based on the mean vehicle speed in the same way as the correction amount $\beta 1$.

Step S306 to step S308 are similar to step S104 to step S107 of FIG. 3, so explanations will be omitted.

Note that, at step S305, the fuel consumption rate correcting part 43 may correct the first fuel consumption rate F1. In this case, the fuel consumption rate correcting part 43 raises the first fuel consumption rate F1 calculated at step S101. At this time, the fuel consumption rate correcting part 43 increases the correction amount of the first fuel consumption rate F1 the greater the mean vehicle speed.

For example, the fuel consumption rate correcting part 43 adds a positive correction amount $\beta 3$ to the first fuel consumption rate F1. At this time, the fuel consumption rate correcting part 43 increases the correction amount $\beta 3$ the greater the mean vehicle speed. The correction amount $\beta 3$ is set in the same way as the correction amount β1 based on the mean vehicle speed. Note that, the fuel consumption rate correcting part 43 may multiply a correction amount β4 greater than "1" with the first fuel consumption rate F1. The correction amount β4 is set in the same way as the correction amount β1 based on the mean vehicle speed.

Further, at step S305, the fuel consumption rate correcting part 43 may correct the first fuel consumption rate F1 and the second fuel consumption rate F2. In this case, the fuel consumption rate correcting part 43 uses the above-mentioned method to raise the first fuel consumption rate F1 and lower the second fuel consumption rate F2. At this time, the fuel consumption rate correcting part 43 enlarges the total of the correction amount of the first fuel consumption rate F1 and the correction amount of the second fuel consumption rate F2 the greater the mean vehicle speed. Further, the control routine of FIG. 6 can be changed in the same way as the control routine of FIG. 3.

Examples

The change in the driving mode when changing the set conditions of the driving mode of the hybrid vehicle to make the hybrid vehicle drive at a low speed was simulated. In this simulation, a hybrid vehicle having the configuration shown in FIG. 1 was used.

Figure 8:
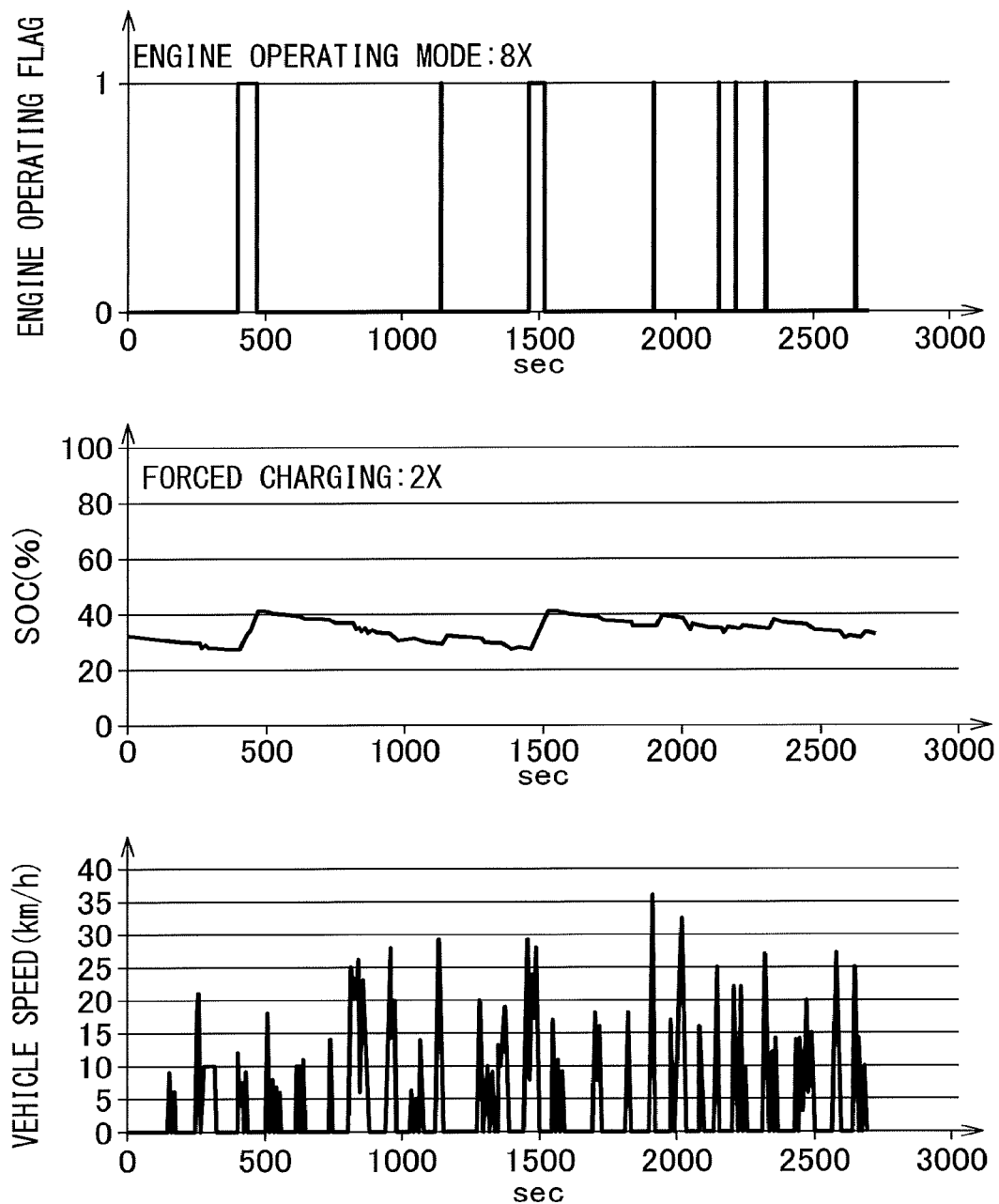
FIG. 8 shows the results of simulation of Comparative Example 1 in which the driving mode is set based on the speed of the hybrid vehicle and driving output demanded by the driver.

FIG. 8 shows the results of simulation of Comparative Example 1 in which the driving mode is set based on the speed of the hybrid vehicle and the driving output demanded by the driver. In Comparative Example 1, basically, the EV mode is selected preferentially as the driving mode when the hybrid vehicle is being driven at a low speed.

FIG. 8 shows a time chart of the engine operating flag, state of charge SOC of the battery, and speed of the hybrid vehicle. The change in vehicle speed was set envisioning the hybrid vehicle driving through a residential neighborhood. The engine operating flag was set to "1" when the driving mode was set to the engine operating mode and was set to "0" when the driving mode was not set to the engine operating mode.

In the results of simulation of Comparative Example 1, the engine operating mode was intermittently selected as the driving mode eight times. That is, intermittent operation of the internal combustion engine was performed eight times. Further, forced charging of the battery occurred two times when the state of charge SOC fell to the threshold value. Note that, if forced charging occurs, the driving mode is forcibly set to the engine operating mode.

FIG. 9 shows the results of simulation of Comparative Example 2 where the fuel consumption rate used for setting the driving mode is not corrected. In Comparative Example 2, the driving mode was set to the EV mode when the first fuel consumption rate of the internal combustion engine when outputting power for driving use was higher than the second fuel consumption rate of the internal combustion engine when storing electric power in the battery, and the driving mode was set to the engine operating mode when the first fuel consumption rate was lower than the second fuel consumption rate. Further, in Comparative Example 2, the first fuel consumption rate and the second fuel consumption rate were not corrected regardless of the speed of the hybrid vehicle.

FIG. 9 shows a time chart of the first fuel consumption rate, the second fuel consumption rate, the engine operating flag, the state of charge SOC of the battery, and the speed of the hybrid vehicle. The change of vehicle speed of FIG. 9 is the same as the change of the vehicle speed of FIG. 8.

In the results of simulation of Comparative Example 2, the engine operating mode was intermittently selected as the driving mode 18 times. That is, intermittent operation of the internal combustion engine was performed 18 times. Further, forced charging of the battery did not occur.

FIG. 10 shows the results of simulation of the Example where the fuel consumption rate used for setting the driving mode is corrected. In the Example, in the same way as Comparative Example 2, the driving mode was set to the EV mode when the first fuel consumption rate was higher than the second fuel consumption rate, while the driving mode was set to the engine operating mode when the first fuel consumption rate was lower than the second fuel consumption rate. Further, in the Example, unlike Comparative Example 2, the second fuel consumption rate was corrected. Specifically, the correction amount β1 set using a map such as shown in FIG. 7 is subtracted from the second fuel consumption rate.

FIG. 10 shows a time chart of the first fuel consumption rate, corrected second fuel consumption rate, engine operating flag, battery state of charge SOC, and speed of the hybrid vehicle. The change of vehicle speed of FIG. 10 is the same as the change of the vehicle speed of FIG. 8.

In the results of simulation of the examples, the engine operating mode was selected intermittently nine times as the driving mode. That is, intermittent operation of the internal combustion engine was performed nine times. Further, forced charging of the battery did not occur.

As a result of the above simulation, in Comparative Example 1, the fuel efficiency became 21.98 km/liter, in Comparative Example 2, the fuel efficiency became 23.53 km/liter, and in the Example, the fuel efficiency became 23.18 km/liter. Therefore, in the Example, it was possible to obtain a fuel efficiency higher than Comparative Example 1 and slightly lower than Comparative Example 2. Further, the frequency of intermittent operation of the internal combustion engine in the Example was smaller than the frequency of intermittent operation of the internal combustion engine in Comparative Example 2 and equal to the frequency of intermittent operation of the internal combustion engine in Comparative Example 1. Therefore, in the Example, it is possible to keep the fuel efficiency of the internal combustion engine from deteriorating while decreasing the noise at the time of driving through a residential neighborhood.

Note that, in this embodiment, when correcting the second fuel consumption rate, the larger the mean vehicle speed of the hybrid vehicle, the larger the correction amount β1 is made. However, similar effects can be expected even if at least one of the first correction raising the first fuel consumption rate and the second correction lowering the second fuel consumption rate is performed.

Above, preferred embodiments according to the present invention were explained, but the present invention is not limited to these embodiments and can be modified and changed in various ways within the language of the claims.

For example, the first motor-generator 12 may be a generator not functioning as a motor. Further, the second motor-generator 16 may be a motor not functioning as a generator. Further, the power distributing mechanism 14 may be mechanically connected to the second motor-generator 16 and the first motor-generator 12 may be omitted. In this case, using the output of the internal combustion engine 10 distributed to the second motor-generator 16, power is generated by the second motor-generator 16, and the generated power is stored in the battery 20. Further, the vehicle 1 may be a plug-in hybrid vehicle enabling charging of the battery 20 from an external power source.

Further, the above-mentioned embodiments can be carried out in any combination. Specifically, the second embodiment can be combined with the third embodiment. In this case, in the control routine of FIG. 6, step S204 of FIG. 5 is performed between step S303 and step S304.

REFERENCE SIGNS LIST 1 hybrid vehicle
10 internal combustion engine
12 first motor-generator
16 second motor-generator
20 battery
40 ECU
41 driving mode setting part
42 fuel consumption rate calculating part
43 fuel consumption rate correcting part
44 driving region judging part

The invention claimed is:

1. A control system of a hybrid vehicle controlling a hybrid vehicle comprising an internal combustion engine and motor able to output power for driving use, and a battery storing electric power generated using output of the internal combustion engine and supplying electric power to the motor, the control system of the hybrid vehicle comprising:
a driving mode setting part configured to set a driving mode of the hybrid vehicle to an EV mode in which an operation of the internal combustion engine is stopped and an output of only the motor is used as power for driving use or an engine operating mode in which the output of the internal combustion engine is used as power for driving use;
a fuel consumption rate calculating part configured to calculate a first fuel consumption rate of the internal combustion engine when outputting power for driving use, and a second fuel consumption rate of the internal combustion engine when storing electric power in the battery;
a fuel consumption rate correcting part configured to correct at least one of the first fuel consumption rate and the second fuel consumption rate calculated by the fuel consumption rate calculating part; and
a driving region judging part configured to judge whether the hybrid vehicle is driving through a residential neighborhood, wherein
the driving mode setting part is configured to set the driving mode to the EV mode when the first fuel consumption rate is higher than the second fuel consumption rate, and set the driving mode to the engine operating mode when the first fuel consumption rate is lower than the second fuel consumption rate, and
the fuel consumption rate correcting part is configured to perform at least one of first correction raising the first fuel consumption rate and second correction lowering the second fuel consumption rate if the driving region judging part judges that the hybrid vehicle is driving through a residential neighborhood, and not to perform the first correction and the second correction if the driving region judging part judges that the hybrid vehicle is not driving through a residential neighborhood.

2. The control system of the hybrid vehicle according to claim 1, wherein the fuel consumption rate calculating part is configured to calculate the first fuel consumption rate as an amount of fuel consumption of the internal combustion engine per unit driving output of the hybrid vehicle obtained by only the output of the internal combustion engine, and calculate the second fuel consumption rate as an amount of fuel consumption of the internal combustion engine per unit power for all of the electric power stored in the battery.

3. The control system of the hybrid vehicle according to claim 1, wherein the driving region judging part is configured to judge that the hybrid vehicle is driving through a residential neighborhood if a mean vehicle speed of the hybrid vehicle when the hybrid vehicle has driven over a predetermined distance is equal to or less than a predetermined value.

4. The control system of the hybrid vehicle according to claim 2, wherein the driving region judging part is configured to judge that the hybrid vehicle is driving through a residential neighborhood if a mean vehicle speed of the hybrid vehicle when the hybrid vehicle has driven over a predetermined distance is equal to or less than a predetermined value.

5. The control system of the hybrid vehicle according to claim 1, further comprising a time-of-day judging part configured to judge a time of day when the hybrid vehicle is being driven, wherein
the fuel consumption rate correcting part is configured to perform at least one of the first correction and the second correction if the driving region judging part judges that the hybrid vehicle is driving through a residential neighborhood and the time of day judged by the time-of-day judging part is early morning or late night, and not to perform the first correction and the second correction if the driving region judging part judges that the hybrid vehicle is not driving through a residential neighborhood or if the time of day judged by the time-of-day judging part is not early morning and late night.

6. The control system of the hybrid vehicle according to claim 2, further comprising a time-of-day judging part configured to judge a time of day when the hybrid vehicle is being driven, wherein
the fuel consumption rate correcting part is configured to perform at least one of the first correction and the second correction if the driving region judging part judges that the hybrid vehicle is driving through a residential neighborhood and the time of day judged by the time-of-day judging part is early morning or late night, and not to perform the first correction and the second correction if the driving region judging part judges that the hybrid vehicle is not driving through a residential neighborhood or if the time of day judged by the time-of-day judging part is not early morning and late night.

7. The control system of the hybrid vehicle according to claim 3, further comprising a time-of-day judging part configured to judge a time of day when the hybrid vehicle is being driven, wherein
the fuel consumption rate correcting part is configured to perform at least one of the first correction and the second correction if the driving region judging part judges that the hybrid vehicle is driving through a residential neighborhood and the time of day judged by the time-of-day judging part is early morning or late night, and not to perform the first correction and the second correction if the driving region judging part judges that the hybrid vehicle is not driving through a residential neighborhood or if the time of day judged by the time-of-day judging part is not early morning and late night.

8. The control system of the hybrid vehicle according to claim 4, further comprising a time-of-day judging part configured to judge a time of day when the hybrid vehicle is being driven, wherein the fuel consumption rate correcting part is configured to perform at least one of the first correction and the second correction if the driving region judging part judges that the hybrid vehicle is driving through a residential neighborhood and the time of day judged by the time-of-day judging part is early morning or late night, and not to perform the first correction and the second correction if the driving region judging part judges that the hybrid vehicle is not driving through a residential neighborhood or if the time of day judged by the time-of-day judging part is not early morning and late night.

9. The control system of the hybrid vehicle according to claim 1, wherein the fuel consumption rate correcting part is configured to increase a correction amount of the corrected fuel consumption rate the larger the mean vehicle speed of the hybrid vehicle when the hybrid vehicle has driven over a predetermined distance.

10. The control system of the hybrid vehicle according to claim 2, wherein the fuel consumption rate correcting part is configured to increase a correction amount of the corrected fuel consumption rate the larger the mean vehicle speed of the hybrid vehicle when the hybrid vehicle has driven over a predetermined distance.

11. The control system of the hybrid vehicle according to claim 3, wherein the fuel consumption rate correcting part is configured to increase a correction amount of the corrected fuel consumption rate the larger the mean vehicle speed of the hybrid vehicle when the hybrid vehicle has driven over a predetermined distance.

12. The control system of the hybrid vehicle according to claim 4, wherein the fuel consumption rate correcting part is configured to increase a correction amount of the corrected fuel consumption rate the larger the mean vehicle speed of the hybrid vehicle when the hybrid vehicle has driven over a predetermined distance.

13. The control system of the hybrid vehicle according to claim 5, wherein the fuel consumption rate correcting part is configured to increase a correction amount of the corrected fuel consumption rate the larger the mean vehicle speed of the hybrid vehicle when the hybrid vehicle has driven over a predetermined distance.

14. The control system of the hybrid vehicle according to claim 6, wherein the fuel consumption rate correcting part is configured to increase a correction amount of the corrected fuel consumption rate the larger the mean vehicle speed of the hybrid vehicle when the hybrid vehicle has driven over a predetermined distance.

15. The control system of the hybrid vehicle according to claim 7, wherein the fuel consumption rate correcting part is configured to increase a correction amount of the corrected fuel consumption rate the larger the mean vehicle speed of the hybrid vehicle when the hybrid vehicle has driven over a predetermined distance.

16. The control system of the hybrid vehicle according to claim 8, wherein the fuel consumption rate correcting part is configured to increase a correction amount of the corrected fuel consumption rate the larger the mean vehicle speed of the hybrid vehicle when the hybrid vehicle has driven over a predetermined distance.

* * * * *